United States Patent [19]

Lantzsch et al.

[11] Patent Number: 4,626,594
[45] Date of Patent: Dec. 2, 1986

[54] PROCESS FOR THE PREPARATION OF BETA-HYDROXYETHYL-(1,2,4-TRIAZOLE) DERIVATIVES

[75] Inventors: Reinhard Lantzsch, Leverkusen; Karl-Julius Reubke, Cologne, both of Fed. Rep. of Germany

[73] Assignee: Bayer Aktiengesellschaft, Leverkusen, Fed. Rep. of Germany

[21] Appl. No.: 672,767

[22] Filed: Nov. 19, 1984

[30] Foreign Application Priority Data

Nov. 25, 1983 [DE] Fed. Rep. of Germany ....... 3342692

[51] Int. Cl.$^4$ .......................................... C07D 249/08
[52] U.S. Cl. ................................................... 548/262
[58] Field of Search ........................................ 548/262

[56] References Cited

U.S. PATENT DOCUMENTS 4,414,210 11/1983 Miller et al. ..................... 548/262

FOREIGN PATENT DOCUMENTS 0040345 11/1981 European Pat. Off. ............ 548/262
0052424 5/1982 European Pat. Off. ............ 548/262
2920374 11/1980 Fed. Rep. of Germany ...... 548/262
3102588 8/1981 Fed. Rep. of Germany .
3018865 11/1981 Fed. Rep. of Germany .
3202604 8/1983 Fed. Rep. of Germany .

OTHER PUBLICATIONS

Kirk–Othmer, Encyclopedia of Chemical Technology, vol. 16, (Second edition, John Wiley & Sons, 1968), pp. 852–853, TP9, E68.

Primary Examiner—Raymond Richard L.
Attorney, Agent, or Firm—Sprung Horn Kramer & Woods

[57] ABSTRACT

Known β-hydroxyethyl-(1,2,4-triazole) derivatives of the formula

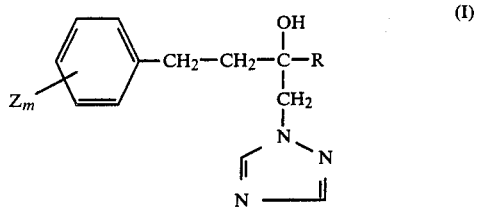

in which
R represents alkyl, halogenoalkyl, optionally substituted cycloalkyl or optionally substituted phenyl,
Z represents halogen, alkyl, cycloalkyl, alkoxy, alkylthio, halogenoalkyl, halogenoalkoxy, halogenoalkylthio, optionally substituted phenyl, optionally substituted phenoxy, optionally substituted phenylalkyl or optionally substituted phenylalkoxy and
m represents the number 0, 1, 2 or 3, are prepared by a new process, which comprises reacting oxiranes of the formula

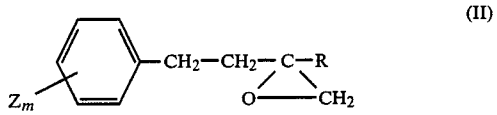

in which R, Z and m have the abovementioned meaning, with 1,2,4-triazole of the formula

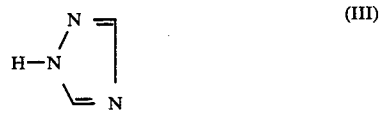

in the presence of a cylcic amid of the formula

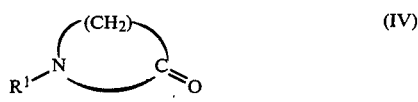

in which
R$^1$ represents alkyl with 1 to 4 carbon atoms and
n represents the number 3, 4 or 5,
as diluent, and in the presence of a base.

9 Claims, No Drawings

PROCESS FOR THE PREPARATION OF BETA-HYDROXYETHYL-(1,2,4-TRIAZOLE) DERIVATIVES

The present invention relates to a new process for the preparation of known β-hydroxyethyl-(1,2,4-triazole) derivatives, which have plant growth-regulating and fungicidal properties.

It has already been disclosed that β-hydroxyethyl-(1,2,4-triazole) derivatives can be prepared by reacting oxiranes with 1,2,4-triazole in the presence of a base and in the presence of inert solvents, such as, for example, methanol, ethanol, n-propanol, acetonitrile or dimethylformamide (compare EP-OS (European Published Specification) No. 30,345, EP-OS (European Published Specification) No. 44,605, EP-OS (European Published Specification) No. 46,337 and EP-OS (European Published Specification) No. 52,424). However, the disadvantage of this process is that, in addition to the 1,2,4-triazole derivatives, greater or smaller amounts of 1,2,4-triazole derivatives are formed, depending on the solvent used. For example, if the reaction is carried out in the presence of alcohols, up to 30% of undesired substances are formed. These troublesome by-products are expensive to remove and the yields of the desired 1,2,4-triazole derivatives are therefore only relatively low. Another disadvantage of this known process is that relatively long reaction times are required.

The present invention now provides a process for the preparation of a β-hydroxyethyl-(1,2,4-triazole) derivative of the formula

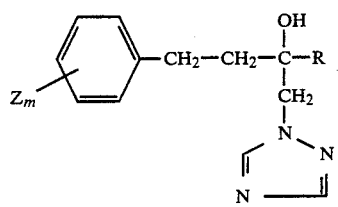

in which
R represents alkyl, halogenalkyl, optionally substituted cycloalkyl or optionally substituted phenyl,
Z represents halogen, alkyl, cycloalkyl, alkoxy, alkylthio, halogenoalkyl, halogenoalkoxy, halogenoalkylthio, optionally substituted phenyl, optionally substituted phenoxy, optionally substituted phenylalkyl or optionally substituted phenylalkoxy and
m represents the number 0, 1, 2 or 3,
which process comprises reacting an oxirane of the formula

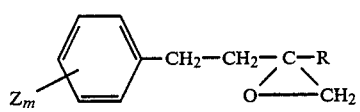

in which R, Z and m have the abovementioned meaning, with 1,2,4-triazole of the formula

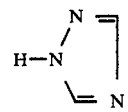

in the presence of a cyclic amide of the formula

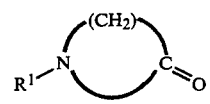

in which
$R^1$ represents alkyl with 1 to 4 carbon atoms and
n represents the number 3, 4 or 5,
as diluent, and in the presence of a base and, if appropriate, in the presence of a co-catalyst and if appropriate in the presence of water, at temperatures between 0° C. and 200° C.

It is to be described as extremely surprising that the β-hydroxyethyl-(1,2,4-triazole) derivatives of the formula (I) can be prepared in higher yields by the process according to the invention than by the method known hitherto. In particular, it was not to be expected that the formation of undesired 1,3,4-triazole derivatives is suppressed, in particular when the reaction is carried out in the presence of cyclic amides of the formula (IV).

The process according to the invention has a number of advantages. Thus, it enables β-hydroxyethyl-(1,2,4-triazole) derivatives of the formula (I) to be prepared in very good yields. In addition, the reaction times are considerably shorter than in the case of the process known hitherto for the synthesis of the compounds of the formula (I). Moreover, isolation of the products which can be prepared according to the invention from the reaction mixture obtained in the reaction presents no difficulties. In particular, no expensive recrystallisation steps are required.

If 2-(4-chloro-phenyl-ethyl)-2-tert.-butyl-oxirane and 1,2,4-triazole are used as starting substances and N-methylpyrrolidone is used as the solvent, the course of the process according to the invention can be illustrated by the following equation:

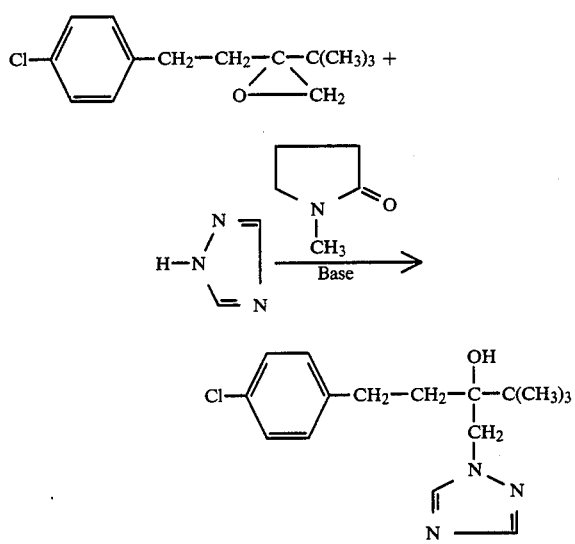

Formula (II) provides a general definition of the oxiranes to be used as starting substances in the process according to the invention. In this formula, R preferably represents straight-chain or branched alkyl with 1 to 4 carbon atoms, straight-chain or branched halogenoalkyl with 1 to 4 carbon atoms and 1 to 5 halogen atoms, cycloalkyl which has 3 to 7 carbon atoms and is optionally substituted by alkyl with 1 or 2 carbon atoms, or phenyl which is optionally mono- or poly-substituted by identical or different substituents, preferred possible substituents being: halogen, alkyl with 1 to 4 carbon atoms and halogenoalkyl with 1 or 2 carbon atoms and 1 to 5 identical or different halogen atoms, such as, in particular, fluorine and chlorine atoms. Z preferably represents halogen, straight-chain or branched alkyl with 1 to 4 carbon atoms, cycloalkyl with 5 to 7 carbon atoms, alkoxy or alkylthio with in each case 1 to 4 carbon atoms, halogenoalkyl, halogenoalkoxy or halogenoalkylthio with in each case 1 or 2 carbon atoms and 1 to 5 identical or different halogen atoms, such as, in particular, fluorine and chlorine atoms, or in each case optionally substituted phenyl, phenoxy or phenylalkyl or phenylalkoxy with 1 or 2 carbon atoms in the alkyl or alkoxy part, preferred substituents which may be mentioned being: halogen and alkyl with 1 to 4 carbon atoms. The index m represents the number 0, 1, 2 or 3, it being possible for the radicals Z to be identical or different.

Particularly preferred compounds of the formula (II) are those in which R represents methyl, isopropyl, tert.-butyl, methyl which is substituted by fluorine and/or chlorine, isopropyl or tert.-butyl, or cyclopropyl which is optionally substituted by methyl, cyclopentyl which is optionally substituted by methyl or cyclohexyl which is optionally substituted by methyl, or phenyl which is optionally mono- or di-substituted by identical or different substituents from the group comprising fluorine, chlorine, methyl and/or trifluoromethyl, Z represents fluorine, chlorine, bromine, methyl, tert.-butyl, cyclohexyl, methoxy, methylthio, trifluoromethyl, trifluoromethoxy or trifluoromethylthio, or phenyl, phenoxy, benzyl or benzyloxy, in each case optionally mono- or di-substituted by identical or different substituents from the group comprising fluorine, chlorine and/or methyl, and m represents the number 0, 1, 2 or 3, it being possible for the radicals Z to be identical or different.

Examples which may be mentioned of oxiranes of the formula (II) are the substances listed by way of their formulae in the following table.

TABLE 1

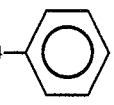

| $Z_m$ | R |
|---|---|
|  4- | —C(CH$_3$)$_3$ |
| 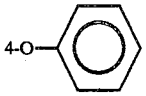 4- | " |

TABLE 1-continued

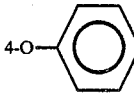

| $Z_m$ | R |
|---|---|
| 4-O—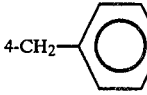 | " |
| 4-O—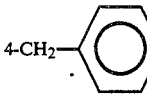—Cl | " |
| 4-CH$_2$—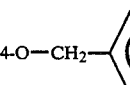 | " |
| 4-CH$_2$—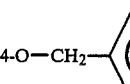—Cl | " |
| 4-O—CH$_2$—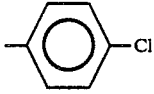 | " |
| 4-O—CH$_2$——Cl | " |
| 3,4-Cl$_2$ | " |
| 4-CF$_3$ | " |
| 4-OCF$_3$ | " |
| 4-SCF$_3$ | " |
| 4-SCH$_3$ | " |
| 4-C(CH$_3$)$_3$ | " |
| 4-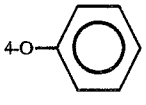 | —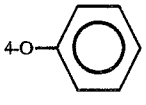—Cl |
| 4-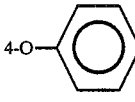—Cl | " |
| 4-O—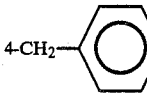 | " |
| 4-O—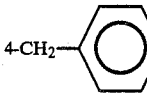—Cl | " |
| 4-CH$_2$—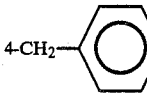 | " |

TABLE 1-continued $$\text{Z}_m-\underset{}{\text{C}_6\text{H}_4}-\text{CH}_2-\text{CH}_2-\underset{\underset{\text{CH}_2}{\text{O}}}{\text{C}}-\text{R} \quad \text{(II)}$$

| $Z_m$ | R |
|---|---|
| 4-CH₂—C₆H₄—Cl | " |
| 4-O—CH₂—C₆H₅ | " |
| 4-O—CH₂—C₆H₄—Cl | " |
| 3,4-Cl₂ | " |
| 4-CF₃ | " |
| 4-OCF₃ | " |
| 4-SCF₃ | " |
| 4-SCH₃ | " |
| 4-C(CH₃)₃ | " |
| 4-C₆H₅ | —CH(CH₃)₂ |
| 4-C₆H₄—Cl | " |
| 4-O—C₆H₅ | " |
| 4-O—C₆H₄—Cl | " |
| 4-CH₂—C₆H₅ | " |
| 4-CH₂—C₆H₄—Cl | " |
| 4-O—CH₂—C₆H₅ | " |
| 4-O—CH₂—C₆H₄—Cl | " |
| 3,4-Cl₂ | " |
| 4-CF₃ | " |
| 4-OCF₃ | " |
| 4-SCF₃ | " |
| 4-SCH₃ | " |
| 4-C(CH₃)₃ | " |
| 4-C₆H₅ | —H |
| 4-C₆H₄—Cl | " |
| 4-O—C₆H₅ | " |
| 4-O—C₆H₄—Cl | " |
| 4-CH₂—C₆H₅ | " |
| 4-CH₂—C₆H₄—Cl | " |
| 4-O—CH₂—C₆H₅ | " |
| 4-O—CH₂—C₆H₄—Cl | " |
| 3,4-Cl₂ | " |
| 4-CF₃ | " |
| 4-OCF₃ | " |
| 4-SCF₃ | " |
| 4-SCH₃ | " |
| 4-C(CH₃)₃ | " |
| 4-C₆H₅ | —C(CH₃)(cyclopropyl ring with CH₃) |
| 4-C₆H₄—Cl | " |

TABLE 1-continued $$\underset{Z_m}{\underset{\|}{\text{Ar}}}-CH_2-CH_2-\underset{O-CH_2}{\overset{R}{C}}\quad (II)$$

| $Z_m$ | R |
|---|---|
| 4-O-C₆H₅ | '' |
| 4-O-(4-Cl-C₆H₄) | '' |
| 4-CH₂-C₆H₅ | '' |
| 4-CH₂-(4-Cl-C₆H₄) | '' |
| 4-O-CH₂-C₆H₅ | '' |
| 4-O-CH₂-(4-Cl-C₆H₄) | '' |
| 3,4-Cl₂ | '' |
| 4-CF₃ | '' |
| 4-OCF₃ | '' |
| 4-SCF₃ | '' |
| 4-SCH₃ | '' |
| 4-C(CH₃)₃ | '' |
| 4-Cl | —CH(CH₃)₂ |
| 4-F | '' |
| 4-CH₃ | '' |
| 4-Cl | —C₆H₁₁ (cyclohexyl) |
| 4-F | '' |
| 4-CH₃ | '' |
| 4-Cl | —C(CH₃)(cyclopropyl) |
| 4-F | '' |
| 4-CH₃ | '' |
| 2,4-Cl₂ | —C(CH₃)₃ |
| 4-CH₃ | '' |
| 4-Cl, 2-CH₃ | '' |
| 2-CH₃ | '' |

The oxiranes of the formula (II) are known, or they can be prepared in a simple manner by known methods (compare EP-OS (European Published Specification) No. 40,345, EP-OS (European Published Specification) No. 46,337 and EP-OS (European Published Specification) No. 52,424).

Formula (IV) provides a definition of the cyclic amides which function as diluents in the process according to the invention.

In this formula, $R^1$ preferably represents methyl or ethyl and n represents the numbers 3, 4 or 5.

Examples which may be mentioned of cyclic amides of the formula (IV) are: N-methyl-pyrrolidone, N-ethyl-pyrrolidone, N-methyl-hexahydro-pyridone and N-methyl-ε-caprolactam.

The cyclic amides of the formula (IV) are already known.

Possible bases for the reaction according to the invention are all the inorganic and organic bases which can customarily be used. These include, preferably, alkali metal carbonates, such as, for example, sodium carbonate and potassium carbonate; alkali metal hydroxides, such as, for example, sodium hydroxide; alkali metal alcoholates, such as, for example, sodium methylate and ethylate and potassium methylate and ethylate; alkali metal hydrides, such as, for example, sodium hydride; and lower tertiary alkylamines, cycloalkylamines and aralkylamines, such as, in particular, triethylamine.

Sodium hydroxide and carbonate and potassium hydroxide and carbonate are particularly preferred.

The process according to the invention is preferably carried out in the presence of a co-catalyst. Possible co-catalysts here are all the compounds which form free radicals. Examples which may be mentioned are azo-bis-isobutyronitrile and benzoyl peroxide. It is also possible to pass air or oxygen through the reaction mixture.

In some cases, it is advantageous to carry out the reaction according to the invention in the presence of a small amount of water, in order thus to achieve better solubility of the base employed.

The reaction temperatures can be varied within a substantial range in carrying out the process according to the invention. In general, the reaction is carried out at temperatures between 0° and 200° C., preferably between 60° and 150° C.

The process according to the invention is in general carried out under normal pressure. However, it is also possible to carry out the reaction under increased or reduced pressure.

In carrying out the process according to the invention, no excess but preferably 1 mole of 1,2,4-triazole and 0.1 to 0.5 mole of base and a sufficient amount of cyclic amide of the formula (IV), as the solvent, are preferably used per mole of oxirane of the formula (II). If a co-catalyst is used, this is added in amounts of 0.01 to 1% by weight, based on the oxirane of the formula (II) employed. If water is used as the auxiliary solvent, only traces of this are added. In general, water is used in amounts of 0.1 to 2% by weight, based on the amount of solvent employed. The reaction according to the invention has in general ended within 2 to 5 hours. The mixture is worked up by customary methods. In general, a procedure is followed in which the reaction mixture is concentrated by distilling off the solvent, and the residue which remains is washed with water and then dried and stirred with an inert organic solvent, such as, for example, petroleum ether or benzine. The product which thereby deposits is separated off and dried again.

The β-hydroxyethyl-(1,2,4-triazole) derivatives of the formula (I) which can be prepared by the process according to the invention are known (compare EP-OS (European Published Specification) No. 40,345). They are distinguished by very good plant growth regulating and fungicidal properties.

The process according to the invention is illustrated by the following examples.

EXAMPLE 1

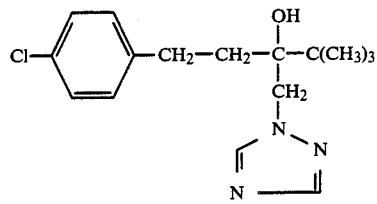
(I-1)

4.15 g (0.103 mole) of sodium hydroxide and a spatula-tip of azo-bis-isobutyronitrile were added to a solution of 71.55 g (0.3 mole) of 2-tert.-butyl-2-(4-chlorophenyl-ethyl)-oxirane in 10 ml of N-methylpyrrolidone. The mixture was heated to 120° C. and a solution of 20.7 g (0.3 mole) of 1,2,4-triazole was added dropwise in the course of 3 hours, with stirring. The mixture was then stirred at 120° C. for a further hour and then allowed to cool. Thereafter, it was worked up by a procedure in which the N-methyl-pyrrolidone was distilled off at a bath temperature of 100° C. under a pressure of 0.2 mbar and the residue which remained was washed with water and then dried and stirred with 150 ml of benzine. The solid product which deposited was filtered off and dried again. 78.9 g (85.8% of theory) of 1-(4-chloro-phenyl)-4,4-dimethyl-3-(1,2,4-triazol-1-yl-methyl)-pentan-3-ol were obtained in this manner.

It was demonstrated by analysis by HPLC that the product is not contaminated by the corresponding 1,3,4-triazole derivative.

EXAMPLE 2

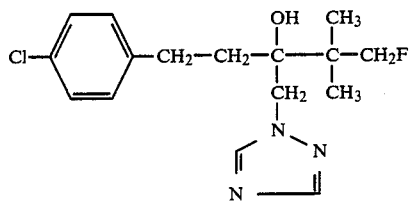
(I-2)

1-(4-Chloro-phenyl)-3-(1,2,4-triazol-1-yl-methyl)-4,4-dimethyl-5-fluoro-pentan-3-ol was obtained by the method described in Example 1, starting from 2-(4-chloro-phenyl-ethyl)-2-(mono-fluoro-tert.-butyl)-oxirane. Yield: 84.7%.

EXAMPLE 3

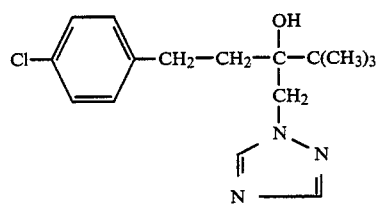
(I-1)

20.7 g (0.3 mole) of 1,2,4-triazole, 4.15 g (0.103 mole) of sodium hydroxide and 1 ml of water were added to a solution of 71.55 g (0.3 mole) of 2-tert.-butyl-2-(4-chloro-phenyl-ethyl)-oxirane in 125 ml of N-methyl-pyrrolidone at room temperature, with stirring. The reaction mixture was heated at 120° C. for 4 hours, with stirring, during which a dry stream of $CO_2$-free air was slowly passed through. Thereafter, the mixture was worked up by a procedure in which the solvent was distilled off under reduced pressure and the residue which remained was washed with water and then dried and stirred with 150 ml of benzine. The solid product which deposited was filtered off and dried again. 81.9 g (88.8% of theory) of 1-(4-chloro-phenyl)-4,4-dimethyl-3-(1,2,4-triazol-1-yl-methyl)-pentan-3-ol were obtained in this manner.

It was demonstrated by analysis by HPLC that the product is not contaminated by the corresponding 1,3,4-triazole derivative.

COMPARISON EXAMPLE

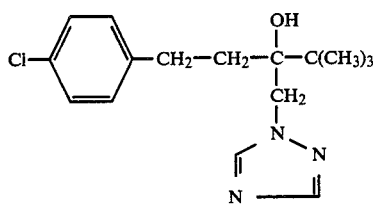
(I-1)

A solution of 27.1 g (0.1 mole) of a product which consisted of 2-(4-chloro-phenyl-ethyl)-2-tert.-butyl-oxirane to the extent of 88%, 8.3 g (0.12 mole) of 1,2,4-triazole and 0.6 g (0.01 mole) of potassium hydroxide in 100 ml of n-propanol was heated at 95° C. for 30 hours. Thereafter, the reaction mixture was allowed to cool and was concentrated by stripping off the solvent under reduced pressure. The residue which remained was taken up in toluene, the suspension thereby formed was filtered and the filtrate was concentrated by stripping off the solvent under reduced pressure. The residue obtained was recrystallised from ligroin. 30.6 g of a product which, according to analysis by HPLC, consisted of 1-(4-chloro-phenyl)-4,4-dimethyl-3-(1,2,4-triazol-1-yl-methyl)-pentan-3-ol to the extent of 67.4% were obtained in this manner. From this, a yield of 67% of theory is calculated.

It will be understood that the specification and examples are illustrative but not limitative of the present invention and that other embodiments within the spirit and scope of the invention will suggest themselves to those skilled in the art.

What is claimed is:

1. A process for the preparation of a β-hydroxyethyl-(1,2,4-triazole derivative of the formula

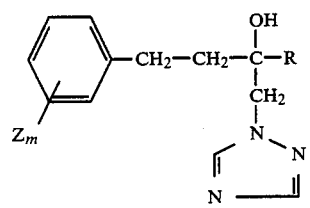

R represents straight-chain or branched alkyl with 1 to 4 carbon atoms, straight-chain or branched halogenoalkyl with 1 to 4 carbon atoms and 1 to 5 halogen atoms, cycloalkyl which has 3 to 7 carbon atoms and is optionally substituted by alkyl with 1 or 2 carbon atoms, or phenyl which is optionally substituted by halogen, alkyl with 1 to 4 carbon atoms and/or halogenoalkyl with 1 or 2 carbon atoms and 1 to 5 halogen atoms, Z represents halogen, alkyl with 1 to 4 carbon atoms, cycloalkyl with 5 to 7 carbon atoms, halogenoalkyl with 1 or 2 carbon atoms and 1 to 5 halogen atoms, halogenoalkoxy with 1 or 2 carbon atoms and 1 to 5 halogen atoms, phenyl which is optionally substituted by halogen and/or alkyl with 1 to 4 carbon atoms, phenoxy which is optionally substituted by halogen and/or alkyl with 1 to 4 carbon atoms, and m represents the number 0, 1, 2 or 3, it being possible for the radicals Z to be identical or different which process comprises reacting an oxirane of the formula

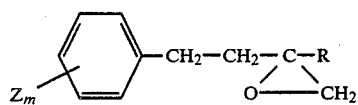

in which

R, Z and m have the abovementioned meaning, with 1,2,4-triazole of the formula

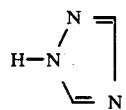

in the presence of a cyclic amide of the formula

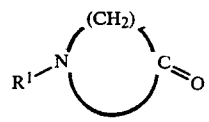

in which $R^1$ represents alkyl with 1 to 4 carbon atoms and n represents the number 3, 4 or 5, as diluent, and in the presence of a base.

2. A process as claimed in claim 1, wherein the reaction is effected in the presence of a co-catalyst selected from azo-bis-isobutyronitrile, benzoyl peroxide, air or oxygen.

3. A process as claimed in claim 1, wherein the reaction is effected in the presence of water.

4. A process as claimed in claim 1, wherein the reaction is effected at a temperature of from 0° C. to 200° C.

5. A process as claimed in claim 4, wherein the temperature is of from 60° C. to 150° C.

6. A process as claimed in claim 1, wherein 2-tert-butyl-2-(4-chloro-phenyl-ethyl)-oxirane is employed as the oxirane.

7. A process as claimed in claim 1, wherein the cyclic amide is a compound in which $R^1$ is methyl or ethyl and n is the number 3, 4 or 5.

8. A process as claimed in claim 7, wherein the cyclic amide employed is N-methyl-pyrrolidone, N-ethyl-pyrrolidone, N-methyl-hexahydropyridone or N-methyl-ε-capro-lactam.

9. A process as claimed in claim 1, wherein the base employed is an alkali metal carbonate, an alkali metal hydroxide, an alkali metal alcoholate, an alkali metal hydride, a lower tertiary alkylamine, a cycloalkylamine or an aralkylamine.

* * * * *